(12) United States Patent
Pelletier

(10) Patent No.: US 6,567,538 B1
(45) Date of Patent: May 20, 2003

(54) REAL TIME MEASUREMENT SYSTEM FOR SEED COTTON OR LINT

(75) Inventor: Mathew G. Pelletier, Lubbock, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/366,220

(22) Filed: Aug. 2, 1999

(51) Int. Cl.$^7$ .................................................. G06K 9/00
(52) U.S. Cl. ....................................... 382/111; 382/224
(58) Field of Search ................................. 382/111, 141; 162/95; 700/130, 142, 143; 356/237.1, 238.1, 238.3; 19/39, 40, 41; 209/509, 539, 546, 580

(56) References Cited

U.S. PATENT DOCUMENTS

| | | | |
|---|---|---|---|
| 5,058,444 A | | 10/1991 | Anthony ....................... 73/866 |
| 5,087,120 A | | 2/1992 | Anthony ....................... 356/36 |
| 5,125,279 A | | 6/1992 | Anthony ....................... 73/866 |
| 5,130,559 A | * | 7/1992 | Leifeld et al. .......... 250/559.11 |
| 5,442,552 A | | 8/1995 | Slaughter ..................... 364/424 |
| 5,544,090 A | * | 8/1996 | Shofner et al. ................ 702/82 |
| 5,639,955 A | * | 6/1997 | Anthony ....................... 73/1.01 |
| 5,805,452 A | | 9/1998 | Anthony ....................... 364/470 |
| 6,040,905 A | * | 3/2000 | Cheng et al. ............. 356/238.3 |
| 6,088,094 A | * | 7/2000 | Chu et al. ................. 356/238.3 |

* cited by examiner

Primary Examiner—Andrew W. Johns
Assistant Examiner—Shervin Nakhjavan
(74) Attorney, Agent, or Firm—John D. Fado; Randall E. Deck

(57) ABSTRACT

A process of utilizing machine vision for processing in a cotton gin monitors a flow of lint and trash anywhere throughout the cotton gin without impeding or detaining product flow, the measurement being made in real time. A video camera or other electronic photography device takes a multi-spectral image of the trash and lint passing through the cotton gin. The multi-spectral image of the trash and lint is partitioned using spectral values into a trash portion, a lint portion, and at least a third image. In turn, at least the image of trash and lint are themselves formed into a binary image from each of the partitioned images. Thereafter, the binary images of the trash portion and the lint portion to determine the ratio of trash to total lint in the flow of lint and trash. The binary image of the trash can be separately processed to determine the relative amounts of sticks, leaves and burrs present in the trash. This enables individual component control in the serial flow through gins and multiple similar components such as incline cleaners, stick cleaners, and lint cleaners. Further, the binary image of the lint can be spectrally analyzed to determine spatial frequency content of the binary image of the lint portion. This spatial frequency content can be utilized to identify color and tinge of the cotton enabling a processing gin to value probable product output in real time.

18 Claims, 16 Drawing Sheets

(2 of 16 Drawing Sheet(s) Filed in Color)

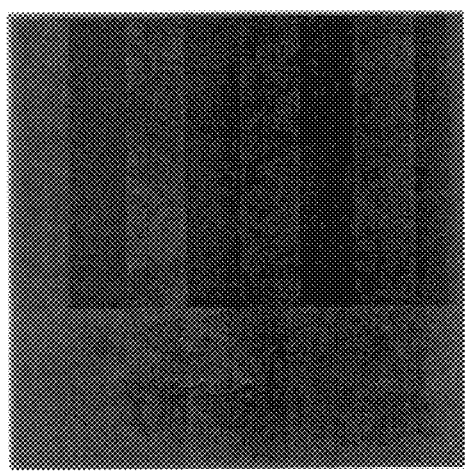
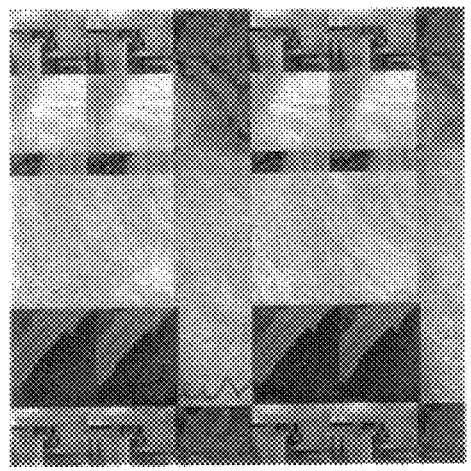
FIG. 9D                                    FIG. 9E

REAL TIME MEASUREMENT SYSTEM FOR SEED COTTON OR LINT

This invention relates to computer/machine vision. More specifically, a system of machine vision is disclosed for the real time measurement of lint and trash being processed in a cotton gin. The system provides the ability to quantify the amount of trash and seed cotton/lint without detaining or impeding the flow through the cotton gin at any time.

The file of this patent application includes at least one color drawing. Copies of this patent application with the color drawing(s) will be provided by the Patent and Trademark Office upon request and payment of the necessary fee.

BACKGROUND OF THE INVENTION

Modem cotton gins have the purpose of extracting lint (the cotton) from trash and seeds- usually the sticks, leaves and burrs that are entrained with the cotton. These modem gins include many individual machine components that are operated sequentially to form the gin processing line. The components are often specific in the types of trash that they remove. Stick machines, inclined cleaners, and especially lint cleaners process the lint to a purity where it can be baled and delivered to spinning mills.

Unfortunately, the cotton processed by such machines varies widely in trash content. For example, stripper harvested cotton has trash content in the range of 30% by total weight of the seed cotton processed, where if the same cotton is stripper harvested with the addition of a field cleaner on the harvester, it may come in with only a 15% trash weight. Even larger trash fluctuations can be observed in regions that are running both stripper and picker harvesters, as the picker harvesters will only have a trash contents in the range of 5%. Due to these different harvesting techniques, the same gin can "see" and process both types of cotton. As a consequence, and depending upon the trash content of the cotton processed, various components of a cotton gin are either left in the serial process combination, or are taken out of the serial process combination. When most cotton gins no longer require their individual components to be configured in series to process cotton for the optimum removal of trash and seed from the lint, the same cotton gin components can also be configured to operate parallel processing lines in order to increase throughput. It is therefore highly desirable to have the cotton gin immediately responsive in its configuration to the trash level of the lint being processed.

It is to be understood that it is customary to over clean the cotton resulting in an economic loss of the valuable line that gets removed at each cleaning apparatus.

Moreover, new growing techniques are also having an impact. For example, new planting techniques utilize ultra narrow rows that can only be harvested with "stripper" harvesters.

It is known that running unnecessarily certain components of a cotton gin can be inefficient to the total economic efficiency of the gin. Trash removed from cotton inevitably extracts lint. And as a general rule, the later in the process the particular piece of cleaning machinery is located, the greater the loss of lint with extracted trash. By way of example, an inclined stick machine placed before ginning of the seed from seed cotton cause lint loss in the range of 0.5%. At the same time, the running of a lint cleaner can cause losses in the range of 20% of the lint. It therefore becomes extremely important to know and understand when a particular component within a cotton gin can be idled while having the output of the gin meet the required quality standard for the ultimately produced lint cotton.

This need to produce a better quality product for sale to the cotton textile mills and to reduce labor costs during processing has led to considerable interest in process control for cotton gins. Anthony and Byler (1994) indicate that process control can range from $15,000 to $100,000. Most of the work to date has involved the online measurement of moisture and trash. Anthony (1990) reported on a system, which used a dynamic programming model along with black and white video trash sensors to determine the optimum number of lint cleaners needed to optimize the returns to the grower.

It is inevitable that the cotton gins in the near future will become fully computerized and automated (Byler and Anthony, 1997). This is due to the fact that optimal control of the gin will produce optimal economic returns for a given ginned bale of cotton (Bennett et al, 1997). This will be advantageous to the growers, the ginners, and the processing mills as they will receive a consistent product that can be tailored to their desired specifications. In this regard, expect the gins to become fully automated in the near future as this technology becomes available. It has already been shown that this automation will utilize some form of trash measurement system at several key locations scattered throughout the ginning process.

Improved machine vision is required. Further, such machine vision will encounter widely varying conditions. For example, the majority of cotton produced in Texas is stripper-harvested. This inexpensive harvesting technique results in large amounts of trash contamination of the seed cotton. The current cleaning techniques present a tradeoff between trash removal and loss of the valuable lint. It has been recognized that adjusting the number of lint cleanings can maximize the profit. The optimum number of lint cleanings can be determined if the trash content and lint turnout is known (Baker, 1994).

One of the major problems facing producers and ginners in the stripper-harvested areas is the presence of large variations in the trash content levels. Additionally the recent innovation of the field cleaner for stripper harvesters has intensified this variation. I feel that this variation leads to a wide range of optimal gin machinery settings for stripper harvested seed cotton cleaning.

Byler and Anthony (1997) reported on a computer-based cotton color and trash measurement system that was used to control the drying and cleaning machinery selection. This system utilizes a global calorimetric color sensor that measures the average color of the imaging area. In addition to the color sensor is a black and white video camera for measurement of the trash particles. A sampling system that presents a solid piece of lint (no voids or holes) and at a uniform packing density to remove the lint shadows is requisite for proper system function. At the time that this system was installed at a gin in Cortland, Ala., it was reported to be the most complete computerized gin process control system in the world. This process control system utilized two trash level sensors. The cotton color/trash sensors were based upon the High-Volume-Instruments (HVI) that are used in the classing office. The first sensor was located opposite of a ram located in the back of the feed control. The ram was periodically extended to press cotton against a glass sample imaging plate. The second color/trash/moisture measurement station was located behind the gin stand and before the lint cleaners. A paddle sampler was used to obtain a sample from the duct and press the sample against a viewing window.

Anthony (1989) reported that sample compression against an imaging window was used to increase the sample density in order to produce a more repeatable image by minimizing the shadows. The coefficient of determination was reported to be r2=0.62 and r2=0.72 for the two trash measurement stations located at the feed control. The sample compression was felt to be important enough that several devices were developed to accomplish this and U.S. Pat. No. 5,125,279 Jun. 30, 1992 entitled System for Analyzing Cotton was obtained for a paddle sampler to accomplish the sample compression for the trash, moisture and color measurement. It is still in use to date in the Zellweger Uster Intelligin and was reported to be fully functional in two commercial gin's as conducted in a USDA study (Anthony et al, 1995).

The modem classing methods use High-volume-Instruments (HVI) systems to measure trash content and lint color. A composite instrument measures the trash content and the lint color. The composite instrument is composed of a black and white video camera for the trash content determination and a two color-filtered silicon based optical sensor to measure the two components used in the classing system: brightness (Rd) and yellowness (+b). Analysis of a two-dimensional black and white image is used to express the percent of the surface area covered by non-lint particles. The algorithm is based upon applying a reflectance threshold to the image. This turns the image into a binary image composed of only two classes, the first class composed of the lint and the second class composed of everything else: trash, holes etc (Thomasson, et al. 1997).

By carefully placing a sample on an HVI instrument with care taken to avoid voids in the samples (that will be miss-classified as trash) the system works reasonably well. However, for an automated on-line system this may not always be the case. As such this technique has the disadvantage in its inability to separate the trash from any holes that may appear in the sample when pressed up against the glass imaging plate. This results in an increased error in the measurement.

Another disadvantage to this technique is the need for pressing the cotton against a glass plate, as this restricts the possible locations where this technique can be applied in a cotton gin in addition to the very likely possibility of stoppage/blockage of the cotton flow due to system malfunctions.

In the following prior art, pressing of lint and/or seed cotton, and trash to avoid the presence of voids has been practiced.

Xu, for pressed lint cotton (note no seed cotton here) was able to show, using multi-spectral values how to partition or label pixels into the following categories or classes: spots, trash, and shadow. Xu, recognized that by the transformation to the CIE L*C*h* color space, he could use the L* value to separate the lint pixels from the trash pixels. Furthermore by using the C* value lint could be separated from spot and trash pixels. Xu realized that a simple discriminant function could be built utilizing a threshold of both L* and C* to partition the space into four regions. He thereby combined the two separations to provide the ability to distinguish and uniquely identify lint pixels, spot pixels, trash pixels, and shadow pixels.

Further analysis of the Xu discrimination technique reveals that although this technique is suitable for its intended purpose, it can not be used in the case where the background shows through the lint. Using simple threshold discrimination of two variables yields at most four possible states. All four of the possible states given the Xu discriminant function have been used by in the identification. The four possible states that can and are used in the Xu discriminate function are lint pixels, spot pixels, trash pixels, and shadow pixels. All of the possible states are accounted for, which leaves no available partitioning in which to assign a new variable to account for background pixels. See *Chromatic Image Analysis for Cotton Trash and Color Measurements*, Xu et al., Textile Res. J, 67(12), 881–890 (1997).

Leiberman reported the ability for shape discrimination for trash into the groups: bark, sticks, or leaves/pepper trash after partitioning the pixels into trash or lint pixels in black and white image via a threshold technique.

Occlusion of multiple light beams has also been used to measure mass flow in both 2 and 3 dimensions. The disadvantage to this technique is the inability to differentiate trash from the lint particles and the associated mass versus volume differences, which are on the order of 100% or more difference by weight. This can be readily shown through the simple observation that dried leaf particles and cotton lint cover a large area with a minimal amount of weight, yet sticks and burrs cover much smaller areas yet weigh much more. See, *Evaluation of Learning Vector Quantization to Classify Cotton Trash*, Lieberman et al., Opt. Engr. 36(3), 914–921 (March 1997) and *Predicting Gravimetric Both in Cotton from Video Indigo*, Lieberman et al., U.S.D.A. Paper No. 926052 of Jun. 21–24, 1992.

SUMMARY OF THE INVENTION

A process of utilizing machine vision for processing in a cotton gin monitors a flow of lint/or seed cotton and trash anywhere throughout the cotton gin without impeding or detaining product flow, the measurement being made in real time. A video camera or other electronic digital imaging device takes a digital multi-spectral image of the trash and lint/or seed cotton passing through the cotton gin. The multi-spectral image of the trash and lint/or seed cotton is partitioned using the spectral values into a trash portion, a lint portion, and at least a third image. In turn, at least the image of trash and lint are themselves formed into a binary image from each of the partitioned images. Thereafter, the binary images of the trash portion and the lint/or seed cotton portion are used to determine the ratio of trash to total lint/or seed cotton in the flow of the lint/or seed cotton and trash. The binary image of the trash can be separately processed to determine the relative amounts of sticks, leaves and burrs present in the trash. This enables individual component control in the serial flow of the cotton through gins and multiple similar components such as inclined cleaners, stick machines and lint cleaners. Further, the binary image of the non-shadowed lint can be utilized as an index into the original multi-spectral image so as to derive a multi-spectral image composed solely of non-shadowed lint. This multi-spectral non-shadowed lint image can be used to ascertain the true average color of the cotton lint. The average non-shadowed lint color can then be used to measure the official USDA-AMS cotton color and tinge. Further, the multi-spectral non-shadowed lint image can be spectrally analyzed to determine color magnitude and spatial frequency fluctuations of the lint. This spatial frequency fluctuation of the multi-spectral data, corresponding only to the non-shadowed lint, can be utilized to identify spots of the cotton. By coupling the trash measurement, the color/tinge measurement, with the spot measurements, these techniques provide the necessary technology thereby enabling a processing gin to value probable product output in real time. The machine measurement system can be used virtually anywhere lint and trash flows within a cotton gin including air entraining ducts, dryers, feeding belts, condensers, bat accumulations, the battery condenser, and the final bale.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 9B–9E are expertly classified training sets built upon the multi-spectral data, the feature vector, that are used to obtain the necessary mean and covariance values for each of the features of the feature vector, that are used in the calculations that are used to classify unknown (unclassified) pixels. These training sets are required to be multi-spectral as the feature vector is built on bands from the multi-spectral data for each pixel;

DESCRIPTION OF THE PREFERRED EMBODIMENT

Figure 1:
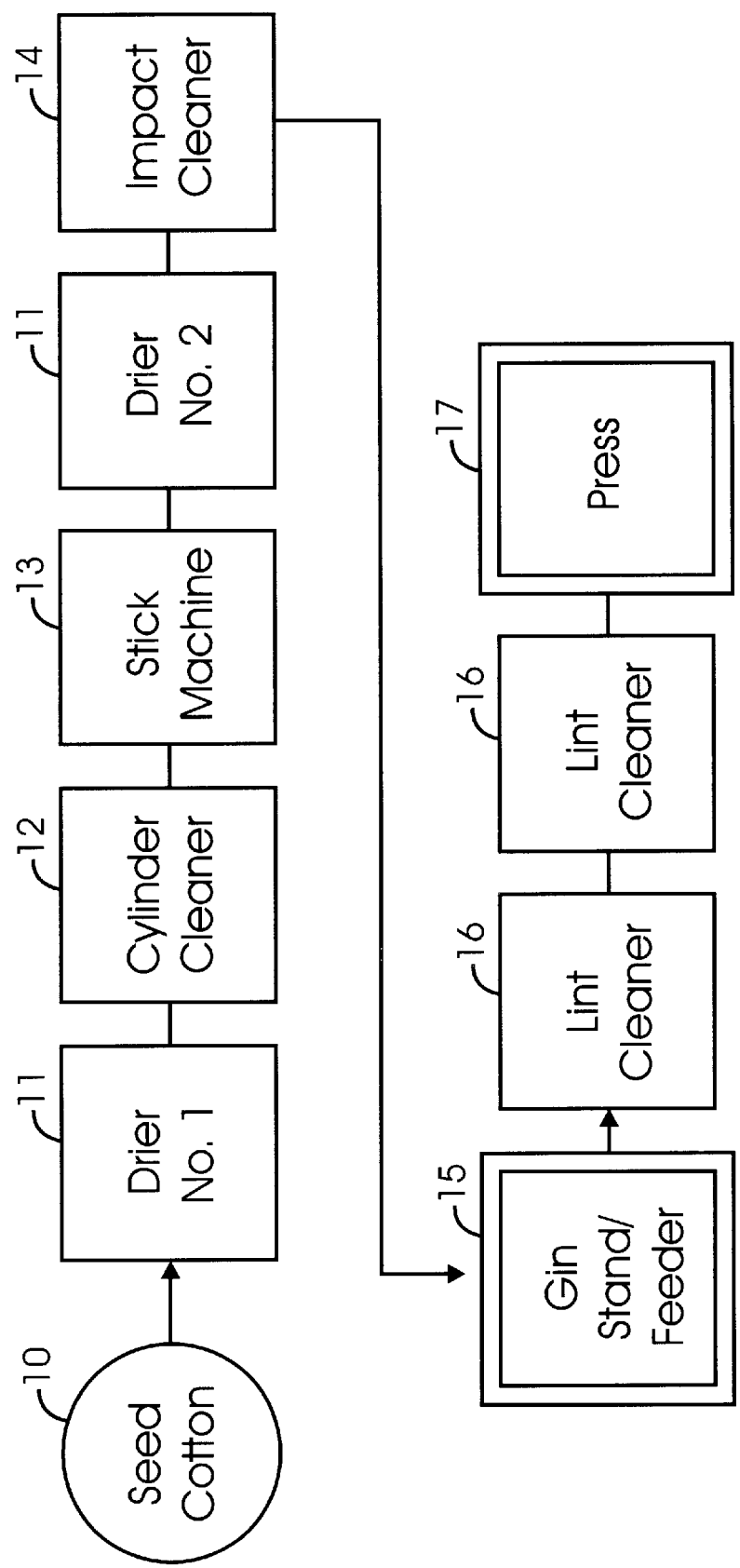
FIG. 1 is a block diagram of seed cotton, trash, and lint flow through a prior art cotton gin.
Figure 2:
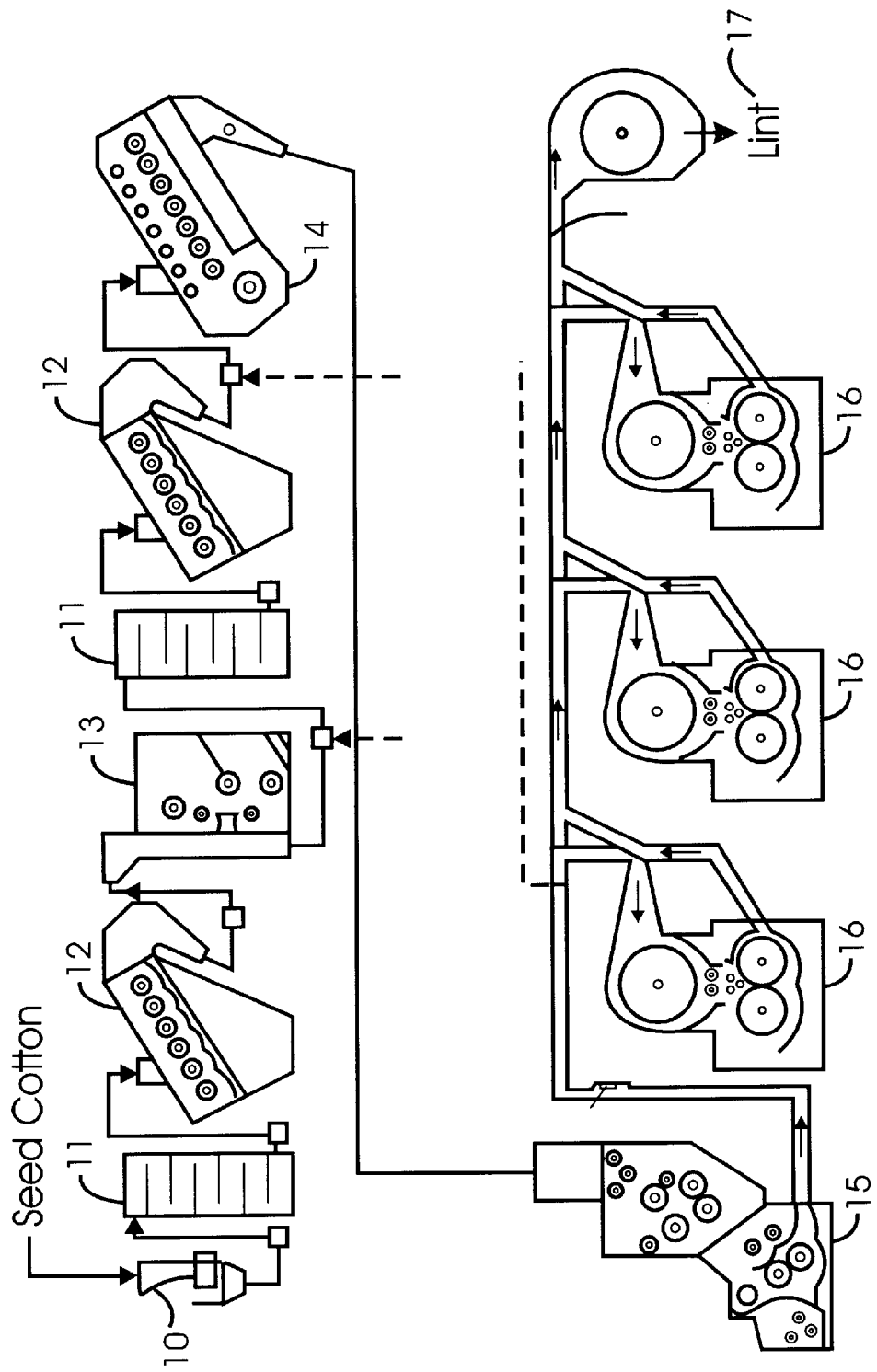
FIG. 2 is a line schematic of the cotton gin illustrated in the block flow diagram of FIG. 1, with exemplary locations for the machine vision of this invention being schematically indicated so that the viewer can understand the broad placement of the vision system here disclosed.

Referring to FIGS. 1 and 2 are simultaneously, a block diagram and line schematic of a "cotton gin." As used herein, the term "cotton gin" encompasses that series of machines, which operated together process seed cotton into baled lint cotton. The apparatus, which separates out the cottonseed from the cotton, will be referred to as the "gin stand." For historical reference of E. Whitney's cotton gin machine for separating cottonseed from lint is in modem usage referred to as the gin stand.

Typically, baled seed cotton 10 is passed through first dryer 11 and in the example here to cylinder cleaner 12. Thereafter, processing at stick machine 13 followed by second dryer 11 occurs. The cotton is then processed at impact cleaner 14 and then to gin stand 15 where seed is removed. Following gin stand 15, lint cleaners 16 process the cotton in series—two such cleaners are shown in FIG. 1 with three such cleaners in series in FIG. 2. At the end of lint cleaners 16, the cotton is baled and further processed as by spinning.

It will be understood that modem storage of raw seed cotton in modules has created a new style of seed cotton entrance into the cotton gin. The old style utilized a suction tube that sucked the cotton out of trailers, while the new system, utilizes raw seed cotton storage into highly compressed modules. The use of the modules requires a machine (module feeder) to break up the cotton from its highly compressed state, into a loose state, one in which it can be properly dried and machined cleaned.

Typically, raw baled seed cotton is fed into the system 10 by module feeder.

We illustrate an exemplary cotton gin. The reader will understand the various gin arrangements are so varied that it is impossible to depict all of the various designs that are in use. Once the raw seed cotton has been fed into the gin, the seed cotton is then passed through first dryer 11 and in the example here to cylinder cleaner 12. Thereafter, processing at stick machine 13 followed by second dryer 11 occurs. The cotton is then processed at impact cleaner 14 and then to gin stand 15 where seed is removed. Following gin stand 15, lint cleaners 16 process the cotton in series—two such cleaners are shown in FIG. 1 with three such cleaners in series in FIG. 2. At the end of lint cleaners 16, the cotton is baled and further processed as by spinning at a separate remote processing plant.

FIGS. 1 and 2 have been taken from Anthony et al. U.S. Pat. No. 5,805,452 issued Sep. 8, 1998 entitled System and Method for Materials Process Control the contents of which are incorporated by reference herein. Simply stated, Anthony et al. makes clear that it is advisable to have visual control over the cotton gin during processing. Specifically, by utilizing only certain components of the cotton gin—say two lint cleaners instead of three lint cleaners, dramatic savings in product output can be obtained. Therefore, just as in Anthony et al U.S. Pat. No. 5,805,452 it is the purpose of this invention to provide machine vision of the processing. This application is restricted to the machine vision itself; we leave to the routineer in view of references like Anthony et al U.S. Pat. No. 5,805,452 the use of the obtained information for the control of the cotton gin.

The machine vision disclosed in Anthony et al U.S. Pat. No. 5,805,452 is limited. Specifically, digital multi-spectral images are not used. Furthermore, cotton flow must be "sampled" by being pressed by a paddle against an imaging and/or glass plate. I seek to expand machine vision in this disclosure. Specifically, and by using and processing a multi-spectral digitized image, I am able to obtain "real time" images of cotton being processed in a cotton gin. The information so obtained can thereafter be used for discrete control of the series connected components of a cotton gin.

It is to be understood therefore, that the machine vision system which I disclose can be used virtually anywhere within the cotton gin disclosed in FIGS. 1 and 2. Location is not restricted to sampling systems such as paddles, rams, and/or compression against glass and/or an imaging plate.

Figure 3:
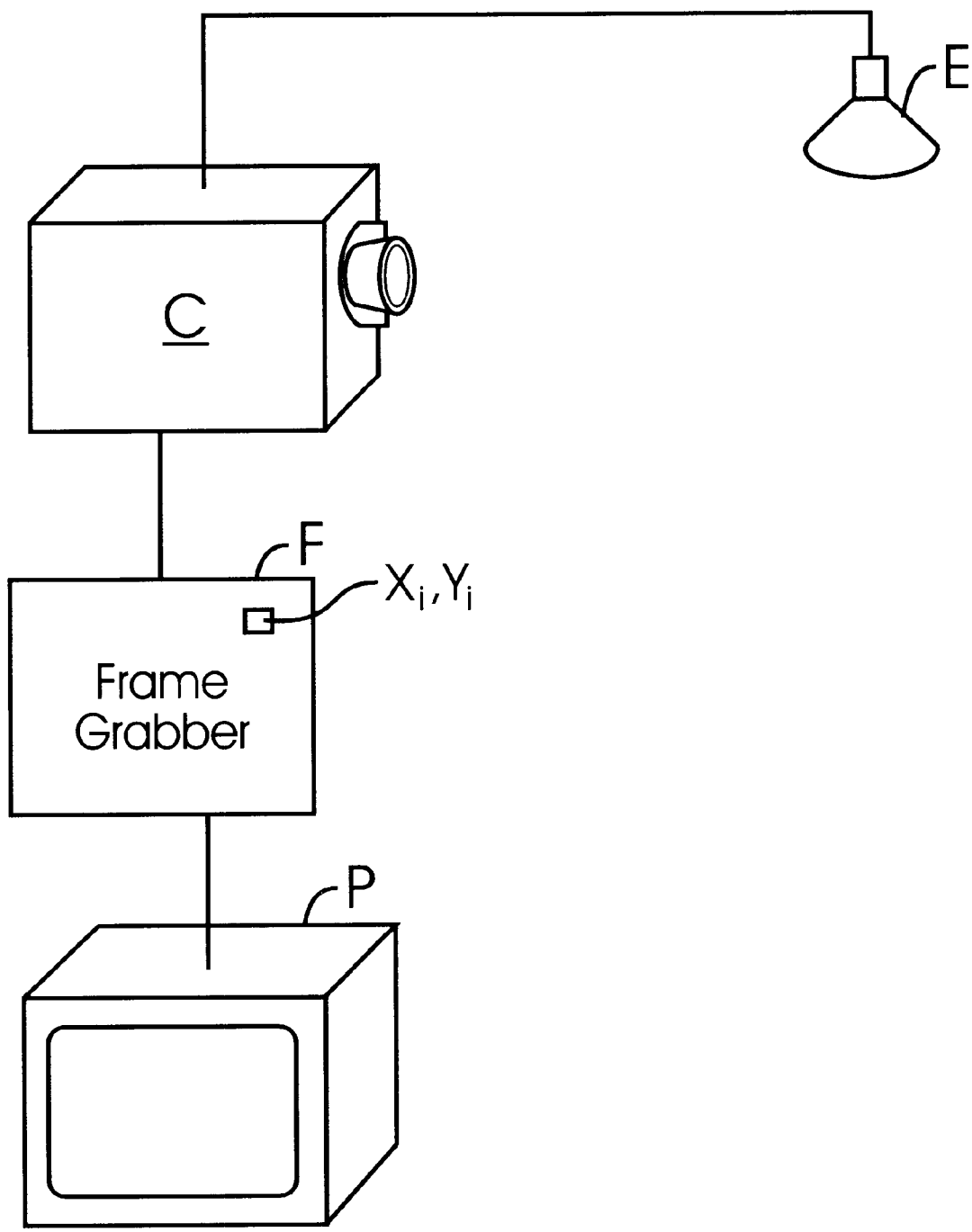
FIG. 3 is a schematic of the hardware used in a typical machine vision station of this invention illustrating the main logical components required for the practice of this invention.

FIG. 3 illustrates a typical machine vision system containing a multi-spectral digital image acquisition system utilized with this invention. The preferred embodiment as outlined in this patent utilizes a Sony XC-003 3 CCD video camera C manufactured by the Sony Corp. of Japan. The frame grabber F to convert the analog image to a digital image is the Matrox Meteor II/Multi-channel RGB frame grabber manufactured by Matrox Electronic Systems ltd. Of Canada. The computer P for performing the necessary digital image processing is a Dell Computer Corporation of United States, model XPS D300 300 Mhz Pentium II with 300 megabytes of ram. Additional hardware can include flash Xenon strobe E lighting to provide for stable and preferred illumination. If required, either and electronic or mechanical shutter H can be provided—dependent upon speed of the moving lint and/or seed cotton and trash.

FIGS. 4A–4D illustrate exemplary places in the cotton gin of FIGS. 1 and 2 where the camera apparatus of FIG. 3 has been placed (and sometimes modified). From these Figures it will be understood that the disclosed machine vision system can virtually be placed at any location where desired.

Figure 4A:
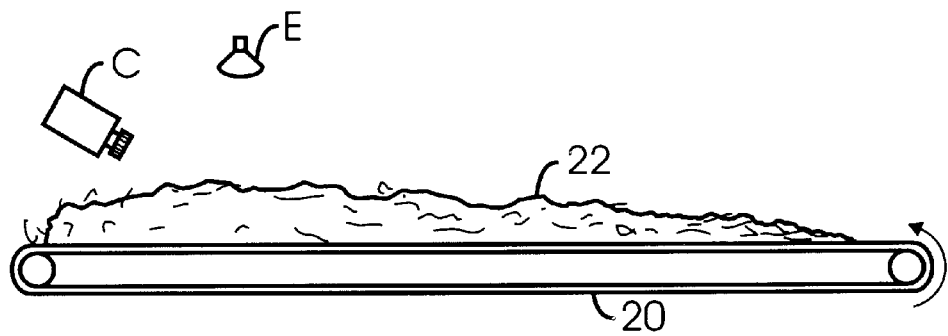
FIG. 4A is an electronic camera for capturing images placed overlying a conveyor belt.

Referring to FIG. 4A, camera C and strobe E are shown overlying conveyor having lint and/or seed cotton 22 thereon.

Figure 4B:
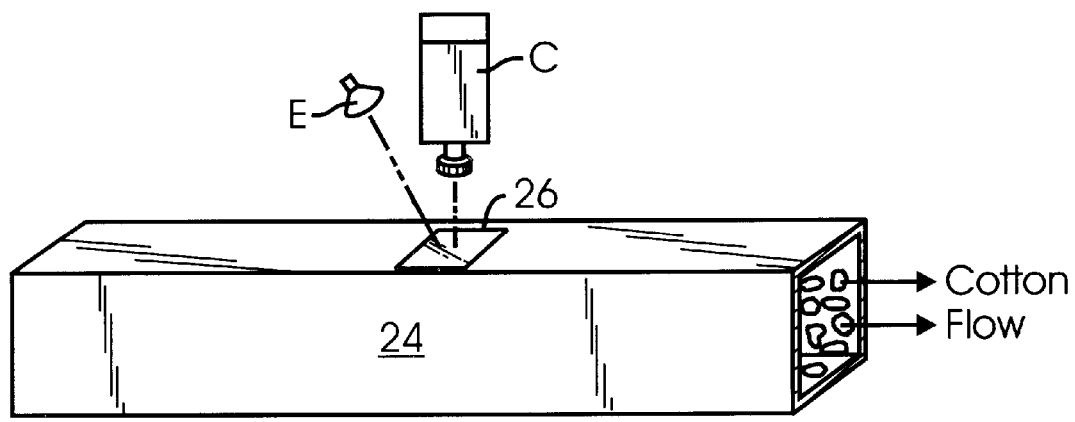
FIG. 4B is an electronic camera for capturing images placed to a duct or dryer for analyzing air entrained lint and trash flow.

In FIG. 4B, camera C and strobe E picture cotton in duct or dryer 24. Where a duct is utilized, either a mechanical or electronic shutter H can be required due to the relative high speed (about 30 mph) of the lint and/or seed cotton and trash.

Figure 4C:
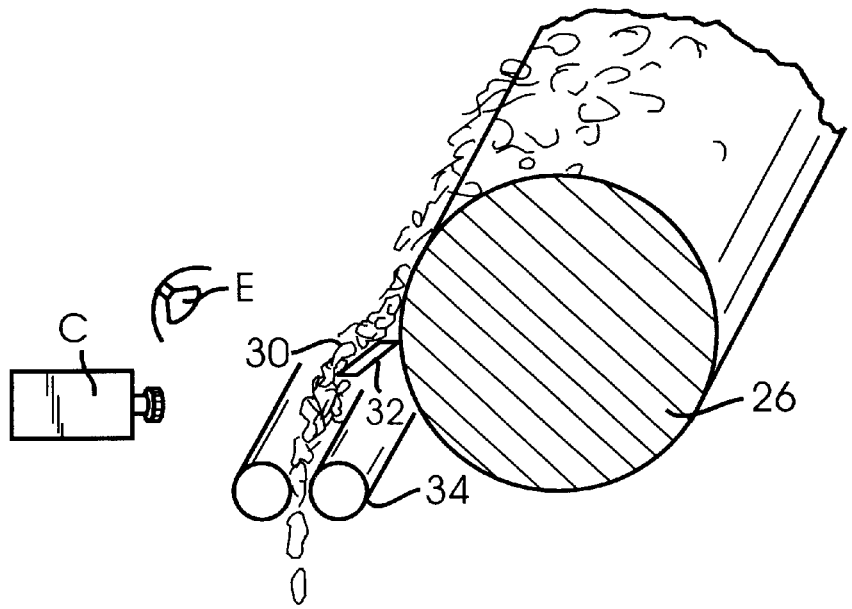
FIG. 4C is an electronic camera for capturing images placed to analyze the lint/seed cotton and trash content of a condenser in a lint cleaner.

In FIG. 4C a typical condenser 26 such as those found in lint cleaners is shown having lint bat 30 extracted by scrapper 32. The bat then passes between feed rolls 34. Camera C and strobe E can be placed anywhere within this illustration and is here shown between the condenser 26 and guide rolls 34.

Figure 4D:
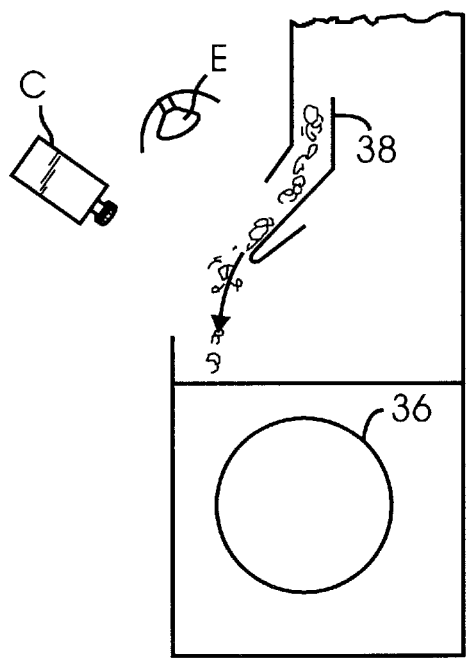
FIG. 4D is an electronic camera for capturing images placed to analyze the lint cotton and trash content on a lint slide leading into the bale press.

In FIG. 4D, camera C and strobe E are placed in gin stand 36 at the entrance of seed cotton 38 to the gin stand. It can be seen that the cotton is falling through the field of vision of camera C into gin stand 36.

Figure 4E:
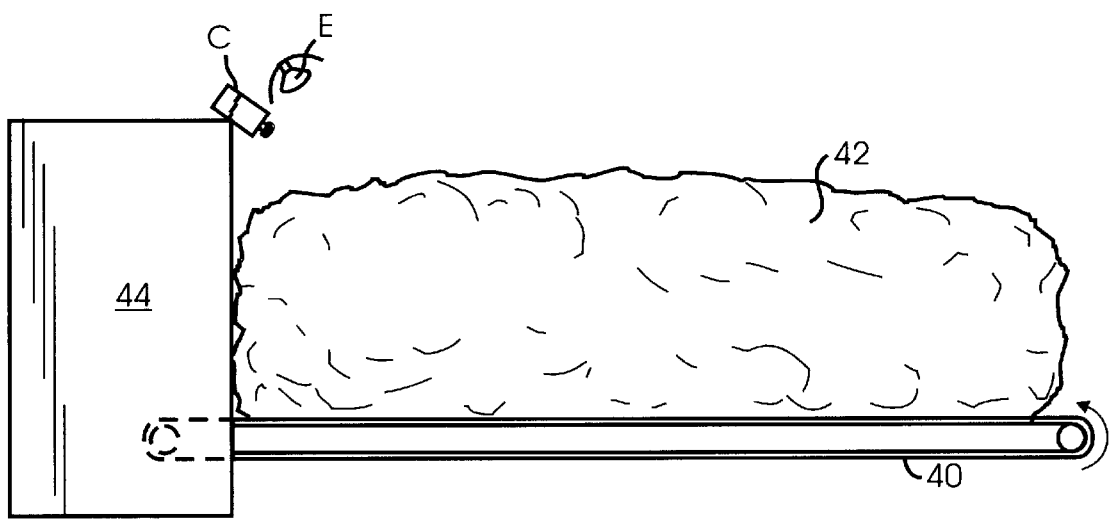
FIG. 4E is an electronic camera for capturing images placed to a module feeder utilized with compressed modules of raw seed cotton.

In FIG. 4E, conveyor 40 conveys a compressed bale of seed cotton 42 into module feeder 44. Camera C and strobe E are shown taking machine vision views of the seed cotton as it is broken away from compressed bale of seed cotton 42.

Figure 5:
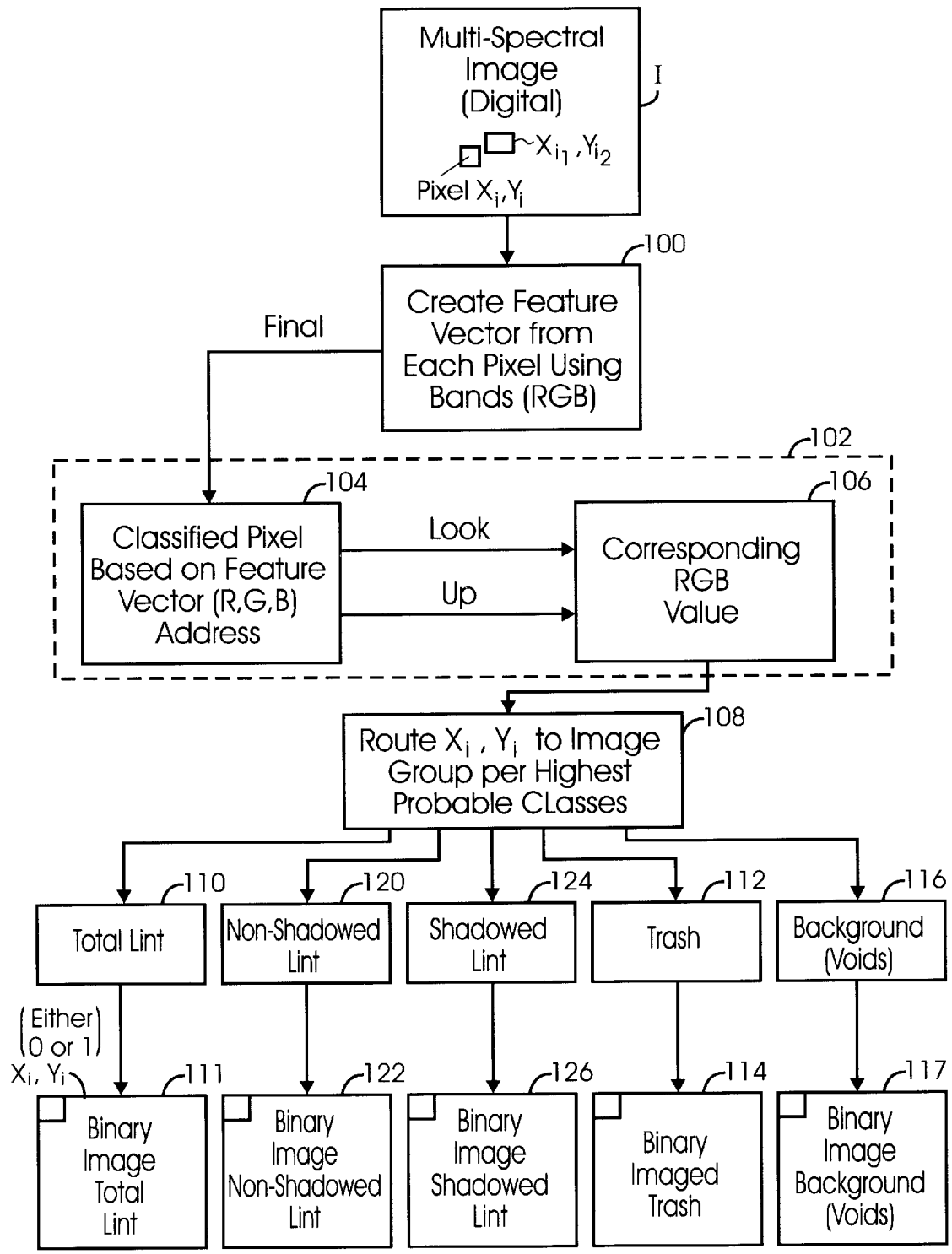
FIG. 5 is a flow chart illustrating the process creating binary images useful for cotton gins from a digital multi-spectral image of lint and/or seed cotton, trash, and voids.

Having set forth the video apparatus and associated processing equipment as well as exemplary locations for the use of this invention, the processing of the multi-spectral image in "real time" can now be set forth. Reference will be made to FIGS. 5–8. Referring to FIG. 5, multi-spectral digital image I is illustrated. This multi-spectral digital image I includes an exemplary pixel $x_i$, $y_i$. By way of example, the total pixel content of multi-spectral digital image I can be in the range of 300,000 pixels with 640 by 480 pixel format. It will be understood that the processing here illustrated refers to the preferred embodiment in which each of the 300,000 pixels are individually and rapidly processed by the disclosed process.

First, and with respect to multi-spectral digital image I, it will be understood that each exemplary pixel contains spectral reflectance information that corresponds to the red, green and blue portion of the visible spectrum, that is red, green, and blue (RGB). Thus, each of pixels $x_i$, $y_i$ holds a discrete value for each of these (primary) colors thereby forming a discrete multi-spectral feature vector [R G B], for each pixel $x_i$, $y_i$.

Each feature vector is in effect a three number vector which is descriptive of the multi-spectral information for pixel $x_i$, $y_i$. This feature vector is then used to calculate the highest probability of the pixel $x_i$, $y_i$ belonging to each of the classes: trash, void (background), non-shadowed lint, lint. The class that contains the highest probability is then chosen as the preferred class to assign pixel $x_i$, $y_i$, as that class represents the highest probability of success for the classification. It should be noted here that in terms of the non-shadowed lint and the lint class, that the non-shadowed lint class is a subset of the lint class, as the lint class is chosen to include both the shadowed and non-shadowed lint. For the case where the class to assign is non-shadowed lint, then two classes are assigned to pixel $x_i$, $y_i$, both the non-shadowed and shadowed lint class.

Bayes decision theory provides a fundamental statistical approach to the problem of pattern classification (Duda et al., 1997). The Bayes classifier is built in terms of a set of discriminant function gi (x), i=1, . . . ,c that seeks to assign a feature vector $x^1$ to one of a finite set of classes (ii by choosing the highest probable class given feature vector x as indicated by the discriminant function gi (x) as in equation 1:

$$g_i(x) > g_j(x) \text{ for all } j \neq i. \tag{1}$$

The classifier computes c discriminant functions and selects the category corresponding to the largest discriminant. The discriminant functions are built around the Bayes formulas:

$$P(\omega_j|x) = p(x|\omega_j)P(\omega_j)/p(x) \tag{2}$$

where:

$P(\omega_j|x)$=α posteriori probability; i.e. the probability of the state being $\omega_j$ given that feature vector x has been measured.

$P(\omega_j)$=probability of the state (or class) $\omega_j$ $p(x|\omega_j)$=conditional probability of feature vector x given state $\omega_j$ $p(x)=\Sigma p(x|\omega_j)P(\omega_j)$=probability of feature vector x (sum over j=1 . . . c).

This approach seeks to classify an unknown entity given feature vector x by minimizing the average probability of error. This is done by selecting the class i that maximizes the a posteriori probability $P(\omega_j|x)$ i.e.

$$\text{Decide class } \omega_i \text{ if } P(\omega_i|x) > P(\omega_j|x) \text{ for all } j \neq i \tag{3}$$

This makes the discriminant function for the minimum error rate classifier:

$$g_i(x) = P(\omega_i|x) \tag{4}$$

$$g_i(x) = p(x|\omega_j)P(\omega_j)/\Sigma p(x|\omega_j)P((\omega_j) \text{ (sum over } j=1 \ldots c). \tag{5}$$

In the two category case (a dichotomizer), the two discriminant functions are lumped into a single equation:

$$g(x)=g_1(x)-g_2(x)=P(\omega_1|x)-P(\omega_2|x) \quad (8)$$

Decide class ω1 if g(x)>0, otherwise decide class ω2.

If we assume that the distribution is Gaussian (or normal) or force the distribution for a given feature to be Gaussian through a transformation, this general multivariate normal density in d dimensions is given as:

$$p(x)=1/[(2\pi)^{d/2}|\xi|^{1/2}]\exp[-\tfrac{1}{2}(x-\mu)'\xi^{-1}(x-\mu)] \quad (6.10)$$

where:

$\mu$=E[x]=expected value of feature vector $x^2$ i.e. d component mean vector $\xi$=E[(x-$\mu$)(x-$\mu$)']

$|\xi|$=d by d covariance[3] matrix $\xi^{-1}$=inverse of the covariance matrix (x-$\mu$)'=transpose of (x-$\mu$)

which leads to the final form for the generalized Bayes Classifier as provided in Equation 6.12 (Duda et al., 1998).

$$g_i(x)=-\tfrac{1}{2}(x-\mu_i)'\xi^{-1}(x-\mu_i)-\tfrac{1}{2}\ln|\xi_i|+\ln P(\omega_i) \quad (6.12)$$

In my preferred embodiment, I utilize this three-numbered feature vector as an address in look-up table 102. Look-up table 102 has been built to hold, for every possible feature vector value, the most probable class for that multi-spectral position In my preferred embodiment, I utilize this three-numbered feature vector as an address in look-up table 102. Look-up table 102 has been built to hold, for every possible feature vector value, the most probable class for that multi-spectral position within the color space. Specifically, feature vectors 104 are [ordered] used as addresses and enable a rapid "look up" of [RGB] the proper class to assign to pixel $x_i$, $y_i$. [value from value portion 106 of look-up table 102. Thereafter, routing of pixel $x_i$, $y_i$ to that image group having highest probability occurs at probability routing step 108]. After assigning the proper class/es, a binary image for each class is built. Set at location $x_i$, $y_i$, in each of the binary images for each class a one if the class assigned to pixel $x_i$, $y_i$, corresponds to the class associated with the binary image, if not leave the pixel value in the binary image a zero. In this manner a set of binary images is built for each of the classes.

Look-up table 102 is comprised of 24 bits of needed address space for a look-up table of 16 megabits capacity. For each and every address, corresponding red, green and blue value of pixel $x_i$, $y_i$, there is a stored class/es in the table. This table starts from RGB value [0 0 0] to [255 255 255].

Exemplary routing destinations are shown. At a minimum, my system requires that total lint 110 contribute to lint image 111, trash 112 contribute to trash image 114, and background 116 contribute to background image 117.

The reader will understand that either through pixel $x_i$, $y_i$ routing or alternately through image addition and/or subtraction, other useful binary images can be constructed. For example, shadowed lint 124 subtracted from total lint 120 can create non-shadowed lint image 122. Thereafter, either routing (as illustrated through shadowed lint 124) or simple image subtraction can create non-shadowed lint image 122. Utilizing only three bits of storage the five representative classes can be mapped into the look-up table, however in practice an eight-bit byte was used for programming convenience.

It is to be understood that over the prior art, my measuring of background image 117 makes possible the real time measurement that I here disclose for trash content. Without such a background measurement, it would not be possible to avoid the step of the prior art where pressing (or discrete sampling) of otherwise flowing cotton would be required. For example, because of the measurement of background or voids, it is possible to use the machine vision system. I disclose at the gin stand feeder apron where cotton is falling through the air and also in a duct within a cotton gin where velocities of cotton movement in the range of 40 feet per second are encountered.

It is to be understood that over the prior art, my measuring of non-shadowed lint/seed cotton, trash and the background makes possible the real time measurement that I disclose here for color measurement. The prior art depends upon a full image window (single pixel) to be filled with cotton, without the removal of the shadowed lint, background, and the large amount of trash found before the gin stand (especially in stripper harvested cotton). From this kind of measurement, large errors as to the determination of the lint color can be evidenced.

Figure 6A:
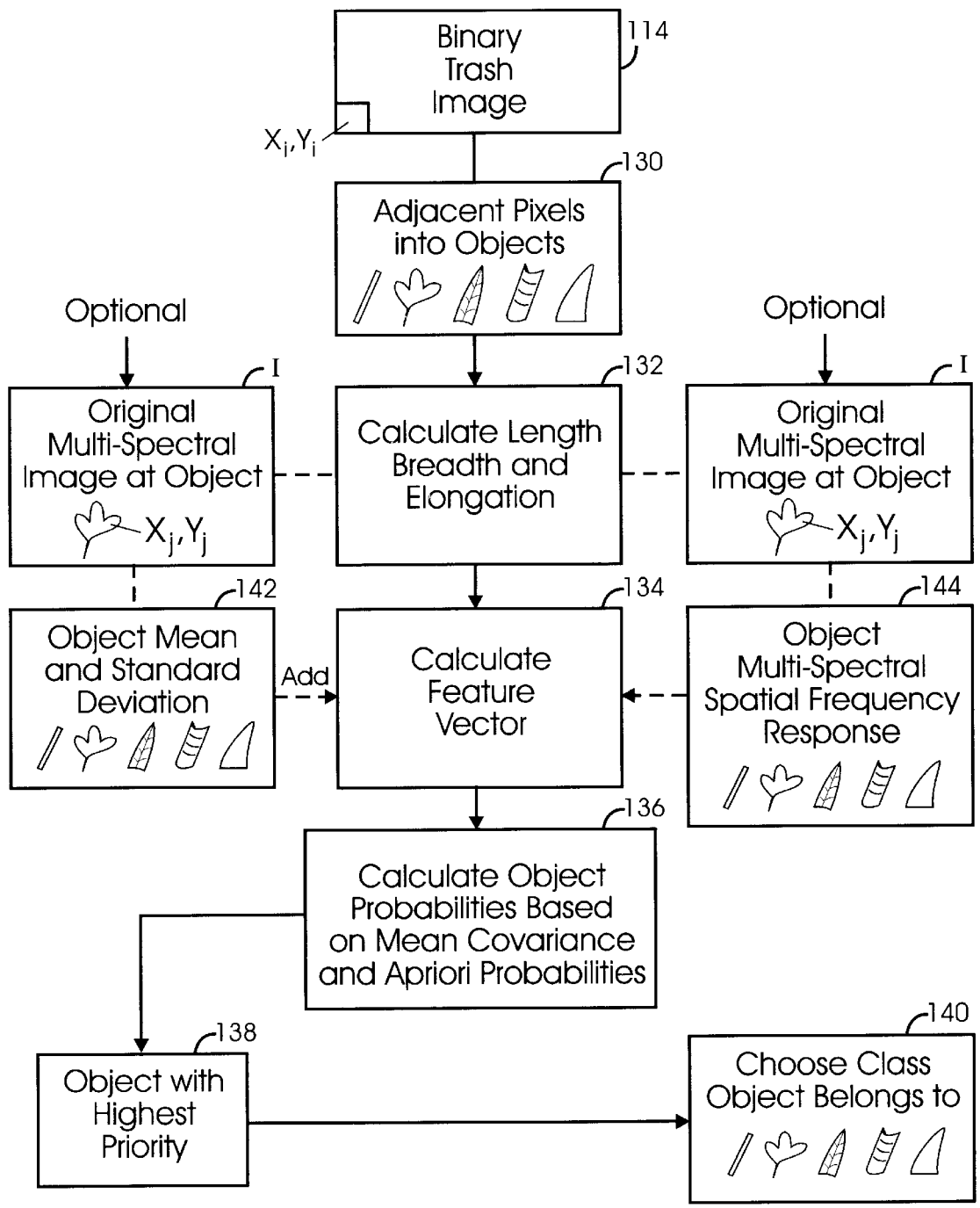
FIGS. 6A and 6B are flowcharts illustrating the processing of the trash binary image for each of sticks, burrs, and leaves; and, FIGS. 7A and 7B are flowcharts illustrating the use of machine vision to calculate total trash content.
Figure 6B:
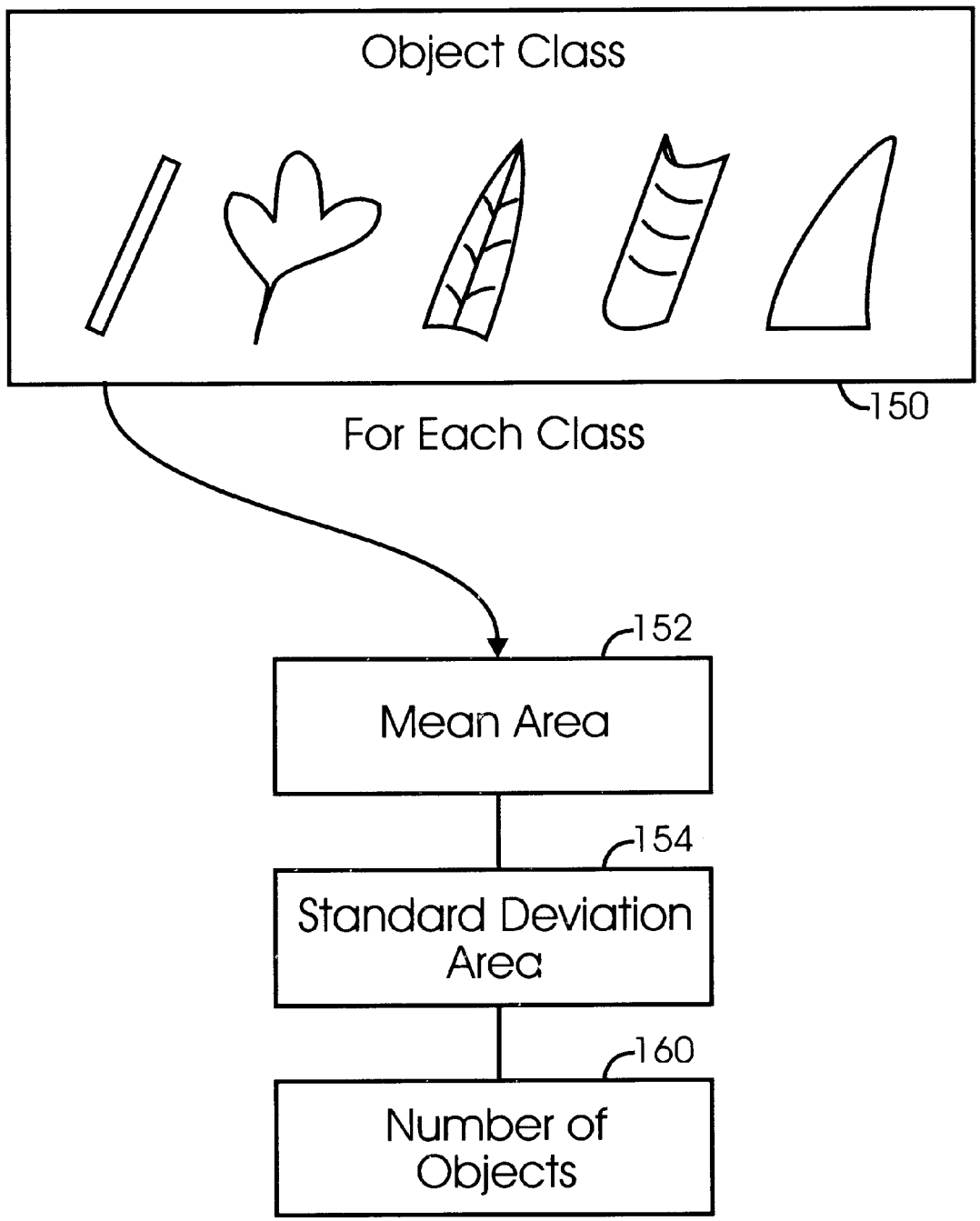

Referring to FIG. 6A, the classification of trash is illustrated. Binary trash image 114 (see FIG. 5) has adjacent pixels grouped into objects step 130. It will be understood that the classes of objects that I seek to find constitute sticks S, leaves L, grass G, bark B, and burrs R.

The analysis of the objects includes calculate length, breadth, and elongation step 132. These geometric parameters make up the feature vector step 134. Utilizing this feature vector calculate object class probabilities step 136 occurs based on the mean, covariance, and α priori probabilities. The step of assigning the class with highest probability to object 140 occurs. In this way build up a set of binary images to represent each of the classes, burrs, bark, sticks, and leaves.

I must point out that feature vector step 134 can be augmented for improved precision. Specifically, and using color information (RGB) multi-spectral digital image I at pixel $x_i$, $y_i$ location, object color mean and standard deviation step 142 can be added to create an augmented feature vector step 134 for greater precision. Additionally and again using multi-spectral digital image I, object multi-spectral spatial frequency response step 144 can likewise augment feature vector step 134. In each case, augmentation occurs by adding on the additional information to increase the discrimination of the discriminant function as acted upon the augmented feature vector.

Next taking the set of binary images for each of the trash components, find the objects average area and standard deviation of object areas within each binary classified image in order to present a set of useful statistics on the trash content to the cotton gin operators.

It will be realized that the trash classification system thus far is relatively elaborate. Total stick area W1, total leaf area W2, total grass area W3, total bark area W4, and total burr area W5 can then all be determined using the information from FIG. 6 and placing this in storage registers schematically located in FIG. 7A. From these discrete calculations, total trash summation step 162 for each class is followed by multiplication by proportionality constant step 164 to obtain total trash step 166.

In order to obtain the necessary comparison of total trash to total cotton, it is necessary to obtain total lint image 111. From this image, calculate total lint area step 170 is followed by multiply by proportionality constant step 172. Utilizing this data, total lint summations step 176 follows.

Having obtained total trash step 166 and total lint summations step 176, the ratio of trash to total lint step 180 occurs. This ratio when multiplied by a proportionality constant step 182 gives total trash content step 184 of cotton being processed.

Figure 7A:
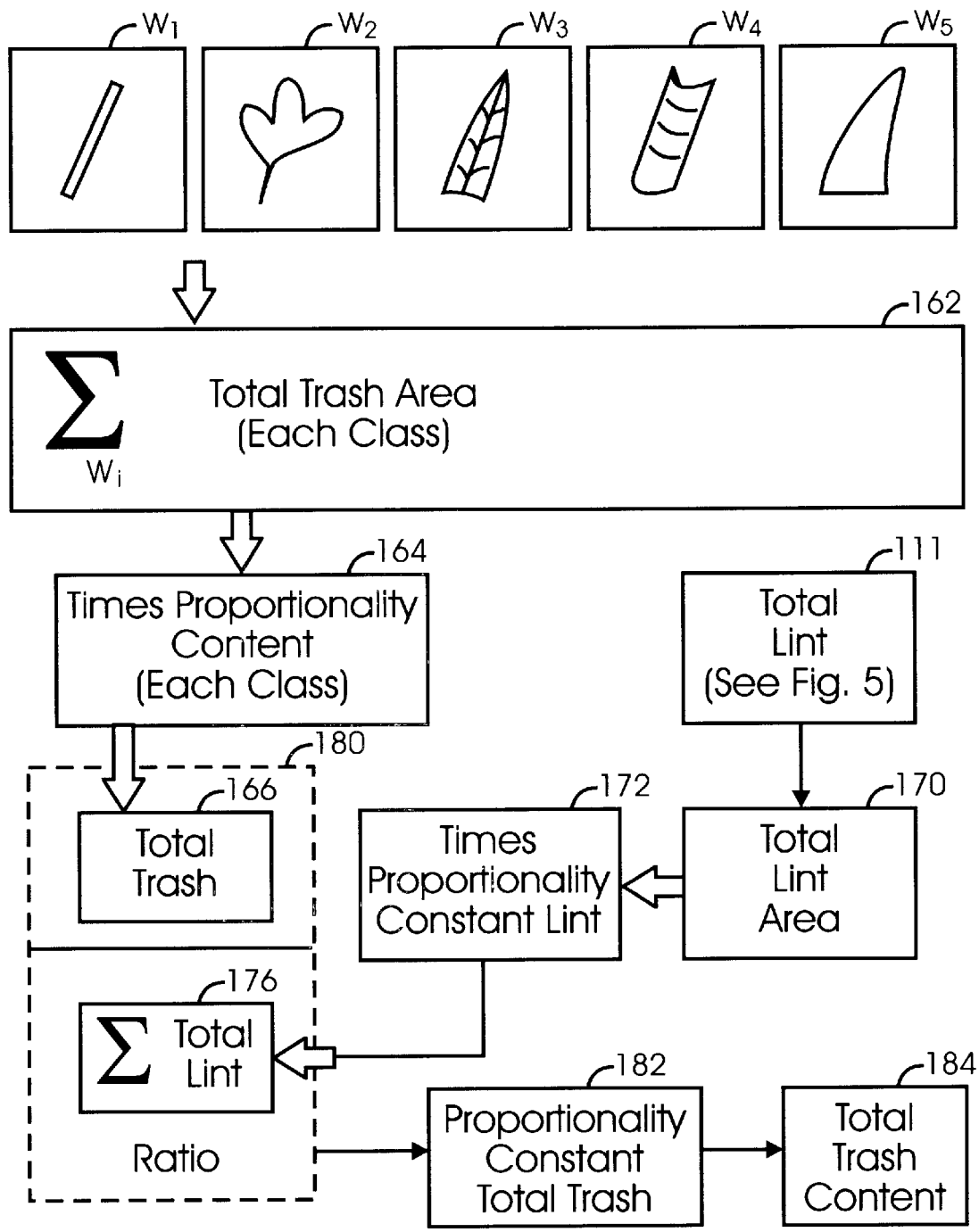
Figure 7B:
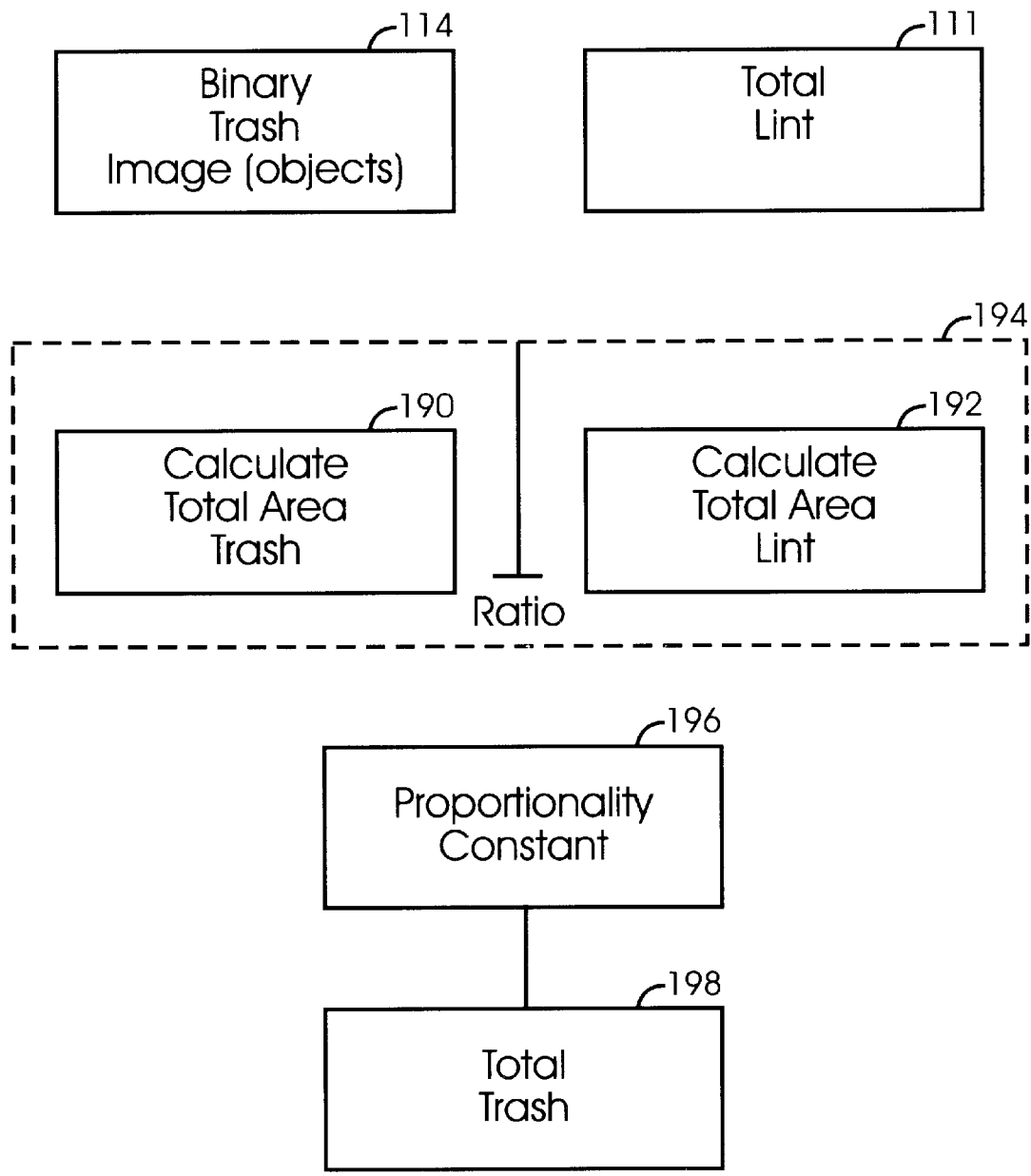

Referring to FIG. 7B, a simpler (but less accurate) method is disclosed for determining total trash. For this process, total lint image 111 and trash image 114 from FIG. 5 are utilized. From these images, calculate total trash area step 190 and calculate total lint area step 192 are carries out. The ratio of these respective areas is obtained at trash to lint ratio step 194. Again, multiplication by proportionality constant step 196 is followed by obtaining total trash content step 198.

Figure 8:
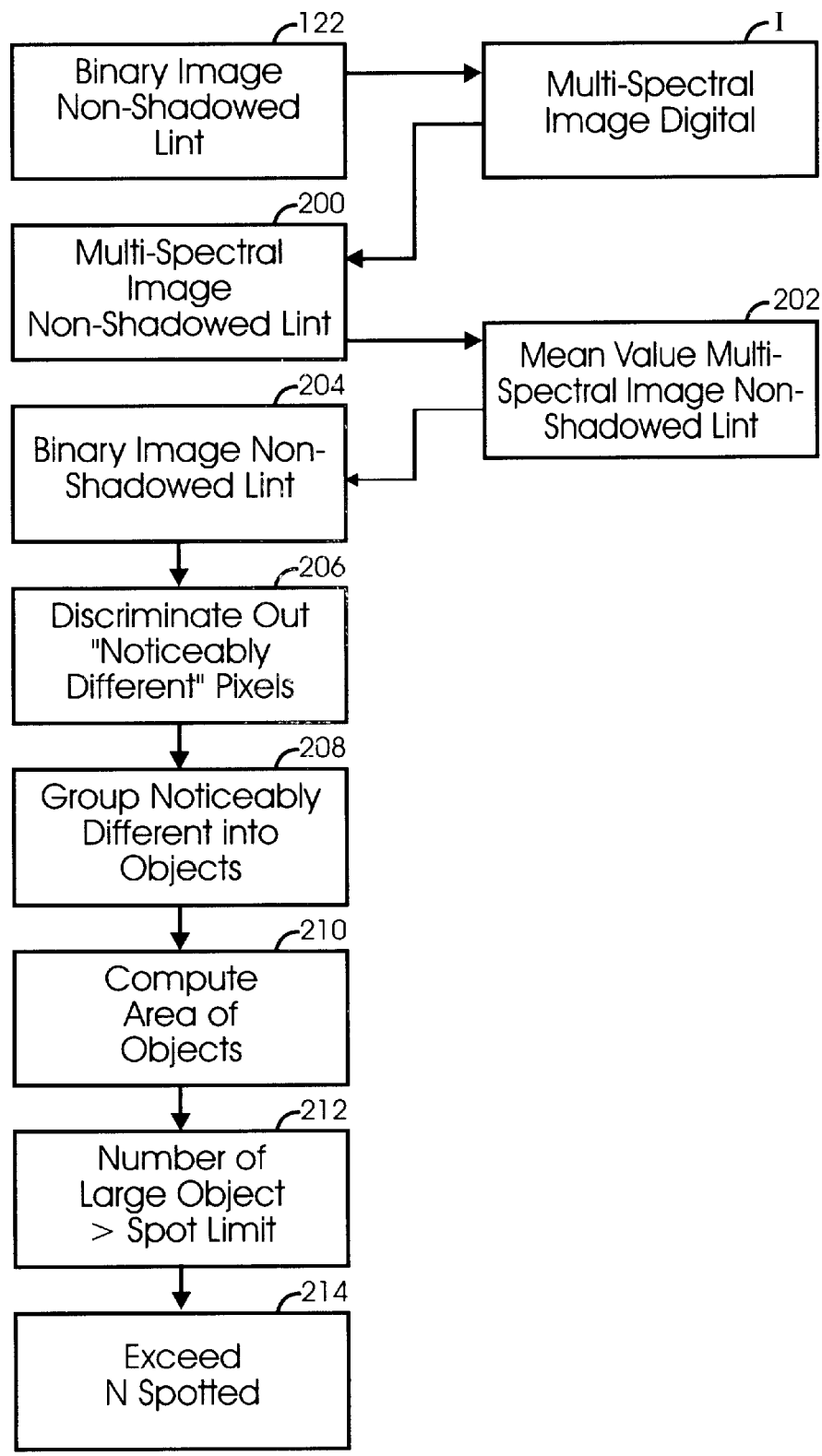
FIG. 8 is a flowchart illustrating accurate color measurement of lint to grade cotton and determine the presence of spotted cotton being processed in a cotton gin.

Referring to FIG. 8, the processing of cotton for determining color and the presence of spotting is disclosed. The process starts utilizing non-shadowed lint image 122. The foot-print of this image is compared to multi-spectral digital image I, and the original color information retrieved for each of the pixel $x_i$, $y_i$. This yields multi-spectral image of non-shadowed lint 200.

The equations for calculating "just noticeable difference", comes in the theory of "color difference measurement". The CIE calorimetric system has a set of recommended equations for the prediction of the magnitude of perceived color difference between two objects (Wyzecki G. and W. S. Styles, 1982).

The technique for color difference measurement lies in the development of a color space transformation that seeks to obtain a color space that has the unique property that any movement within the color space to a new color that is just noticeably different. The just noticeably different view is to the standard observer, is the same distance regardless of direction or position within the color space. This new color space is an approximation to a uniform color space. That is the color space has a uniformity and linearity in regards to color perception. It is a well-known fact, that in the CIE XYZ, and CIE RGB color space this is not the case. A few of the transformations that are recommended by the CIE for the evaluation of color differences are (CIE, 1978): CIE 1976 L*u*v*, and CIE 1976 L*a*b*. For the preferred embodiment we recommend CIE 1976 L*a*b* defined as:

$$L^* = 116(Y/Y_n)^{1/3} - 16$$

$$a^* = 500[(X/X_n)^{1/3} - (Y/Y_n)^{1/3}]$$

$$b^* = 200[(Y/Y_n)^{1/3} - (Z/Z_n)^{1/3}]$$

The total color difference equation is calculated from the measurement of the vectorial distance in this color space as defined as:

$$\Delta E^*_{ab} = [(\Delta L^*)^2 + (\Delta a^*)^2 + (\Delta b^*)^2]$$

The formula $\Delta E$ represents the magnitude of the color difference perceived between two object-color stimuli, which are specified in terms of their CIE tristimulus values. The difference $\Delta E$ is the quantity of importance in industrial color-control problems and in the establishment of color tolerances (Wyzecki G. and W. S. Styles, 1982). It will be understood that by increasing $\Delta E$, the "color distance" is in effect increased. Thus, this standard can be stretched for the particular use desired, in this case the determination of spots in cotton.

In the use of determining when a cotton lint spot is noticeably different, the $\Delta E^*_{ab}$ is calculated and then multiplied by a proportionality constant to tune the system to match the standard cottons that are maintained in the USDA-AMS Memphis vaults. Thus, the equation for use in determining when a pixel would be called a spot pixel or lint pixel is:

If $\Delta E^*_{ab} > k$ then
   call pixel spot
else
   call pixel lint

Alternatives for spot recognition are also present. It should also be recognized that the $\Delta E$ could also be calculated in the Rd and +b color space as well as through the use of many of the various Whiteness formulas. Furthermore, it should be noted however, at this point it appears that the values being used for $X_n$, $Y_n$, $Z_n$, that are used for the conversion to the cotton classing color space Rd and +b, are $Y_n = Z_n = 100$. The Rd and +b color space was developed by Nickerson and Hunter who developed the standard based upon the ICE (currently the CIE) XYZ tristimulus values, corrected for the ICI standard illuminant C (ASTM-D2253, 1973). This standard gives the transformation from the ICE XYZ color space to the official USDA-AMS cotton color space Rd and +b as defined as:

$$Rd = Y + b = 35.7(21 - 20Y/Y_n)/(1 - 20Y/Y_n) * (Y/100 - 0.847Z/Z_n)$$

where:
   Y, Z: XYZ CIE tristimulus values for the two degree observer under the CIE C Illuminant.

Once all such pixels $x_i$, $y_i$ are discriminated out and grouped into objects at discrimination step 206 and object step 208. Thereafter, compute area of objects step 210 is followed by determining objects exceeding given size step 212. At this point, it is only required that the number of spots exceed a determined number (or the size of a particular spot exceed a set size) step 214. This labels the cotton as spotted. Thus, using the output of the spot classified binary image step 202 if the number of spots exceed a determined number or area step 214, lint can be graded as to overall color and the presence of spotting can be determined.

Figure 9A:
FIG. 9A is a seed cotton image which in the practice of this invention must be taken in color.
Figure 9B:
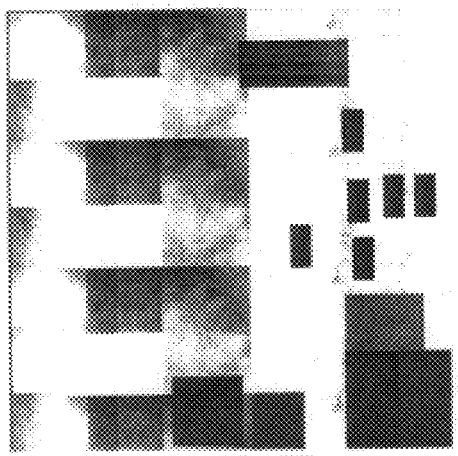
Figure 9C:
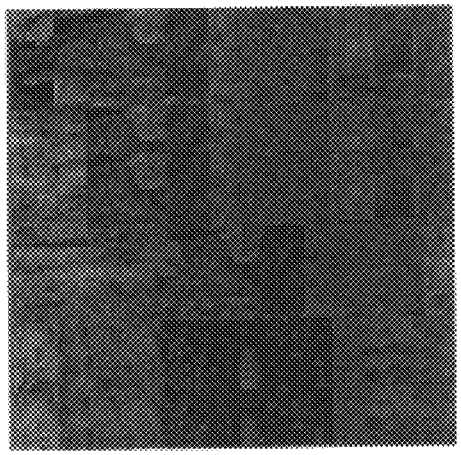

FIG. 9A is a black and white image of a color image of cotton.

FIGS. 9B–9E are composite images of color features for lint, sticks, voids and burrs. They each comprise a sample of expected images manually extracted which are representative of all pixels from that particular class. This constitutes an array of values from which the mean and covariance for each class are calculated. The resultant information can be used to build the classification look up table through the use of the Bayes discriminant function. Dependent upon the general geographic area, these composite images may be required to be customized.

Figure 10A:
FIGS. 10A and 10B are binary images of lint/or seed cotton and trash respectively.
Figure 10B:

FIGS. 10A and 10B have the binary images for cotton and trash respectively.

Figure 11:
FIG. 11 is an object labeled binary trash image depicting the computer's ability to recognize and associate an object for each adjacent pixel groupings. Once the objects have been recognized, then each objects geometric properties are then analyzed for use in the classification of sticks, leaves, burrs, and grass; and, FIG. 12 is a graphical representation of predicted trash relative to actual [percent] trash content (mass basis) which includes the statistical probability (proportion) of the total variation that is explained by the prediction (regression) is greater than 91% with an RMS residual error in prediction better than 2½% trash content utilizing the machine vision system of this invention.

FIG. 11 is a sample of trash images. It will be seen that the vision processing has assigned a discrete processing number, which has been displayed for each "object." This representation has been taken from actual data utilizing the machine vision protocol here shown.

Figure 12:
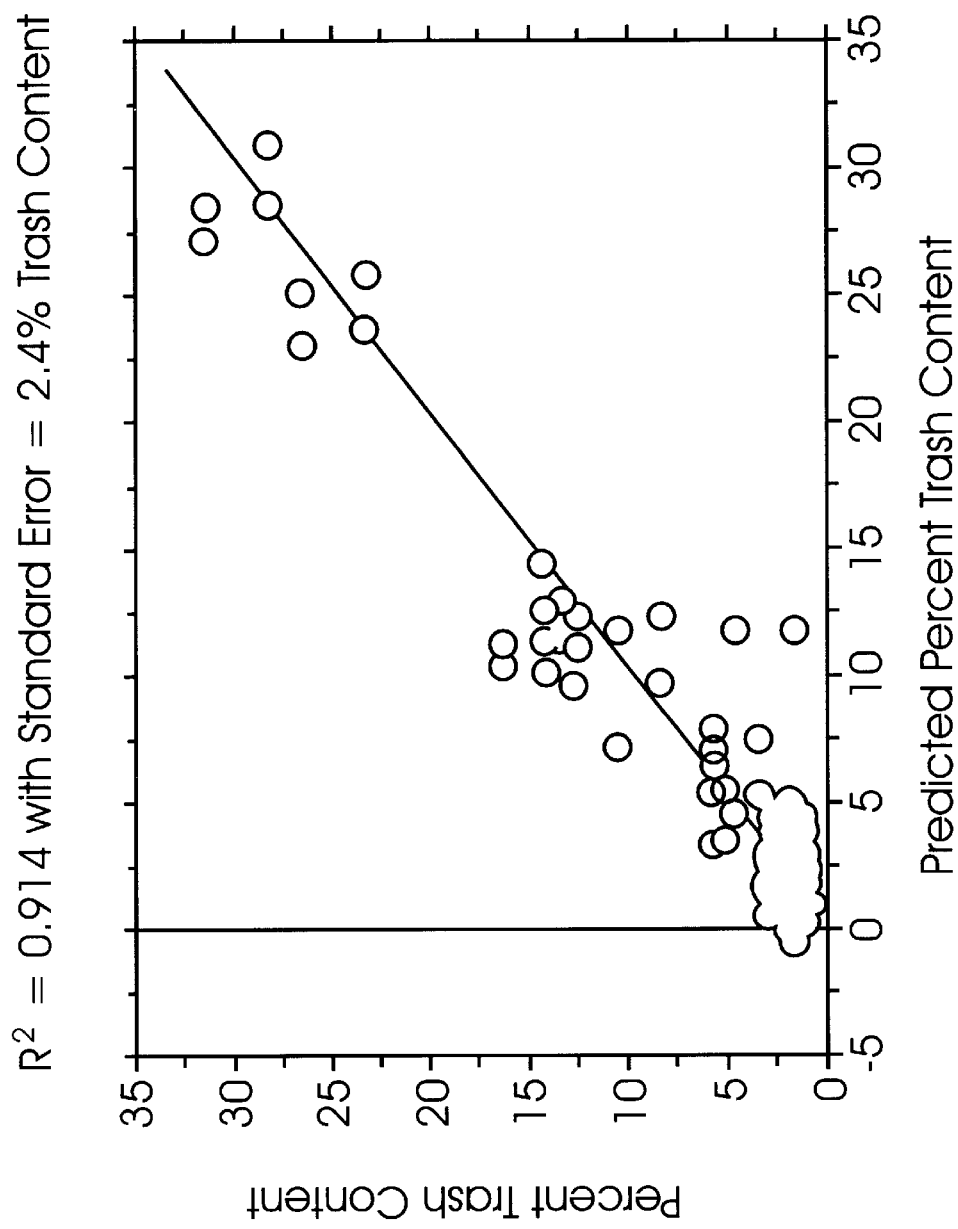

Finally, FIG. 12 is a graphical representation of the trash to lint percentage obtained herein. It shows that the disclosed process is in the order of 91% accurate. This accuracy range is an important advantage of the system here disclosed.

What is claimed is:

1. A process of utilizing machine vision for processing in a cotton gin having a flow of seed cotton, lint and/or trash through the cotton gin comprising the steps of:

providing a multi-spectral digital image of lint and/or seed cotton and trash passing through the cotton gin, the image having discrete pixels;

partitioning the multi-spectral image using spectral values into a trash pixels, lint and/or seed cotton pixels, and void pixels;

creating a binary images from at least the trash pixels and the lint and/or seed cotton pixels; and, utilizing the binary images of the trash pixels and the lint and/or seed cotton pixels to determine a ratio of trash to lint and/or seed cotton in the flow of lint and/or seed cotton and trash.

2. The process of utilizing machine vision for processing in a cotton gin having a flow of lint and/or seed cotton and trash through the cotton gin according to claim 1 and further comprising:

partitioning fourth lint and/or seed cotton in shadows pixels.

3. The process of utilizing machine vision for processing in a cotton gin having a flow of lint and/or seed cotton and trash through the cotton gin according to claim 1 and further comprising the steps of:

analyzing the trash image for sticks, leaves, and burrs.

4. The process of utilizing machine vision for processing in a cotton gin having a flow of lint and/or seed cotton and trash through the cotton gin according to claim 3 and further comprising the steps of:

the analyzing the trash image for sticks, leaves and burrs includes;

grouping adjacent binary pixels in the trash as objects;

measuring the objects with one or more of the parameters selected from the group consisting of length, breadth, elongation, perimeter, area, moment of inertia, and statistical distribution.

5. The process of utilizing machine vision for processing in a cotton gin having a flow of lint and/or seed cotton and trash through the cotton gin according to claim 1 and further comprising the steps of:

analyzing the lint for spots including, utilizing the binary image of lint and/or seed cotton pixels to provide a color image of non-shadowed lint;

determining the mean of the color image of the non-shadowed lint;

determining noticeably different pixels from the mean of the color image of the non-shadowed lint;

grouping the noticeably different pixels into objects;

counting the objects to determine the presence of cotton spotting.

6. A process of utilizing machine vision for processing in a cotton gin having a flow of lint and/or seed cotton and trash through the cotton gin comprising the steps of:

providing a cotton gin having a flow of lint and/or seed cotton and trash;

providing camera for recording a multi-spectral image of lint and/or seed cotton and trash passing through the cotton gin, the multi-spectral image having digital pixels;

recording the multi-spectral image of lint and/or seed cotton and trash without detaining the flow of trash and lint and/or seed cotton through the cotton gin;

partitioning the multi-spectral image using digital spectral values into a trash pixels, a lint and/or seed cotton pixels, and void pixels;

utilizing the trash pixels and the lint and/or seed cotton pixels to determine the ratio of trash to total cotton flow in the flow of cotton and trash.

7. A process of utilizing machine vision for processing in a cotton gin having a flow of cotton and trash through the cotton gin according to claim 6 and wherein:

the flow of lint and/or seed cotton and trash is on a conveyor.

8. A process of utilizing machine vision for processing in a cotton gin having a flow of cotton and trash through the cotton gin according to claim 6 and wherein:

the flow of lint and/or seed cotton and trash is in a dryer.

9. A process of utilizing machine vision for processing in a cotton gin having a flow of cotton and trash through the cotton gin according to claim 6 and wherein:

the flow of lint and/or seed cotton and trash is in a duct having the lint and/or seed cotton and trash entrained within an air flow passing through the duct.

10. A process of utilizing machine vision for processing in a cotton gin having a flow of cotton and trash through the cotton gin according to claim 6 and wherein:

the flow of lint and trash is in and/or just after a condenser.

11. A process of utilizing machine vision for processing in a cotton gin having a flow of cotton and trash through the cotton gin according to claim 6 and wherein:

grouping the trash into objects;

determining the length, breadth and elongation of the objects;

creating a feature vector; and, using the feature vector to classify the objects into at least one object class chosen from the group sticks, leaves, grass, bark, and burrs.

12. A process of utilizing machine vision for processing in a cotton gin having a flow of cotton and trash through the cotton gin according to claim 11 and wherein:

inserting color information to the feature vector.

13. A process of utilizing machine vision for processing in a cotton gin having a flow of cotton and trash through the cotton gin according to claim 12 and wherein:

utilizing the mean and/or standard deviation of the color information.

14. A process of utilizing machine vision for processing in a cotton gin having a flow of cotton and trash through the cotton gin according to claim 12 and wherein:

utilizing the multi-spectral frequency response of the color information.

15. A method of measuring flow of cotton being processed, the cotton including seed, lint and/or seed cotton, and trash, the method comprising the steps of:

generating a multi-spectral image of the cotton flow;

digitizing the multi-spectral image into pixels having multi-spectral reflective values;

providing expertly classed possible values for lint and/or seed cotton, trash, and/or void space;

comparing the pixels having multi-spectral reflectance values to expertly classed possible values to determine whether a pixel represents a pixel of an image of lint and/or seed cotton, a pixel of an image of trash and/or a pixel of an image of void space; and, generating discrete images of lint and/or seed cotton, trash and voids from the comparing of the pixels, wherein the providing expertly classed possible values comprises the further steps of:

obtaining a sample multi-spectral image of lint and/or seed cotton, trash, and voids;

digitizing the sample multi-spectral image to obtain pixels;

generating mean and covariance values based upon the visual characteristics of lint and/or seed cotton, trash, and voids; and, placing the pixels into expertly classed possible values according to the mean and covarience values of lint and/or seed cotton, trash, and voids.

16. A method of determining the color and spotting of cotton lint from a color image of the cotton comprising the steps of:

provi ding a color image of non-shadowed lint;

determining the mean of the color image of the non-shadowed lint;

determining noticeably different pixels from the mean of the color image of the non-shadowed lint;

grouping the noticeably different pixels into objects.

17. A method of determining the color and spotting of cotton lint from a color image of the cotton according to claim 16 and wherein the step of determining the noticeably different pixels from the mean of the color image of the non-shadowed lint includes:

increasing color distance from of the noticeably different pixels from the mean of the color image of the non-shadowed lint.

18. A method of obtaining expertly classed images from visualized cotton being processed including lint and/or seed cotton, trash and voids comprising the steps of:

obtaining a sample multi-spectral image of lint and/or seed cotton, trash, and voids;

digitizing the sample multi-spectral image to obtain pixels;

generating mean and covariance values based upon the visual characteristics of lint and/or seed cotton, trash, and voids; and, placing the pixels into expertly classed possible values according to the mean and coverience values of lint and/or seed cotton, trash, and voids.

* * * * *